United States Patent [19]
Honjo et al.

[11] Patent Number: 5,756,084
[45] Date of Patent: May 26, 1998

[54] HUMAN STROMAL DERIVED FACTOR 1α AND 1β

[75] Inventors: Tasuku Honjo; Michio Shirozu, both of Kyoto; Hideaki Tada, Osaka, all of Japan

[73] Assignee: Ono Pharmaceutical Co., Ltd., Osaka, Japan

[21] Appl. No.: 674,008

[22] Filed: Jul. 1, 1996

Related U.S. Application Data

[62] Division of Ser. No. 323,084, Oct. 14, 1994, Pat. No. 5,563,048.

[30] Foreign Application Priority Data

Oct. 14, 1993 [JP] Japan ................... 5-280505

[51] Int. Cl.$^6$ .................... C07K 14/52; A61K 38/19
[52] U.S. Cl. .................... 424/85.1; 530/324; 514/2; 514/8; 514/12; 435/69.5; 435/71.1; 435/326; 435/172.3; 435/320.1; 435/252.3
[58] Field of Search .................... 530/324; 514/2, 514/8, 12; 424/85.1; 435/69.5, 71.1, 326, 172.3, 320.1, 252.3

[56] References Cited

FOREIGN PATENT DOCUMENTS 0607054  1/1994  European Pat. Off. .

OTHER PUBLICATIONS

Nagasawa et al, *Proc. Natl. Acad. Sci. USA*, 91:2305–2309 (1994).
Bowie et al. (1990) Science, vol. 247, pp. 1306–1310.
Tashiro et al. (1993) Science vol. 261, pp. 600–603.
Derynck et al. (1990) Biochemistry. vol. 29, pp. 10225–10233.
Weissenbach et al. (1980) Proc. Natl. Acad. Sci. vol. 77, No. 12, pp. 7152–7156.

*Primary Examiner*—John Ulm
*Assistant Examiner*—Prema Mertz
*Attorney, Agent, or Firm*—Sughrue, Mion, Zinn, Macpeak & Seas, PLLC

[57] ABSTRACT

The polypeptides of the present invention are produced and secreted in pro-B cells, so they may be used for diseases relating to undergrown or abnormal proliferation of hematopoietic cells, neuronal enhancement or depression, immunological enhancement and depression, for example, inflammatory diseases (rheumatoid arthritis, ulcerative colitis etc.), hematopoietic stemcytopenia after bone marrow transplantation, leukocytopenia, thrombocytopenia, B lymphopenia and T lymphopenia after chemotherapy, anemia, infectious diseases, cancer, leukocytosis, AIDS, neurodegenerative diseases (Alzheimer, multiple sclerosis etc.), prevention of treatment of neuronal injury, prevention of treatment of disorder of bone metabolism (osteoporosis etc.) or tissue repair. The DNA of the present invention may be utilized as an important and essential template in preparing the polypeptides of the present invention which are expected to possess various use or for diagnosis of an in the treatment of gene diseases.

8 Claims, 1 Drawing Sheet

HUMAN STROMAL DERIVED FACTOR 1α AND 1β

This is a Divisional Application of U.S. application Ser. No. 08/323,084, filed Oct. 14, 1994 now U.S. Pat. No. 5,563,048.

FIELD OF THE INVENTION

The present invention is related to novel polypeptides produced by human pro-B cell line and DNAs encoding them.

PURPOSE OF THE INVENTION

The present invention is related to novel polypeptides produced by hematopoietic cells and DNAs encoding them. It is known that many kinds of growth and differentiation factors, such as interleukin (IL), are secreted from hematopoietic cells.

This fact suggests that factors having similar or novel functions might be secreted therefrom in addition to the known factors already found.

The present inventors have paid attention to this point and attempted to find novel factors (polypeptide) produced from hematopoietic cells. The present inventions were screened by cross hybridization using mouse SDF-1 (Stromal Derived Factor 1: described in Japanese Patent Application No. 5-22098) cDNA as a probe to obtain human SDF-1 (2 kinds, β and α) produced from human pro-B cells.

When polypeptides having sequences identical or highly homologous with that of the polypeptide of the present invention and the DNAs encoding them are searched for with a computer, none are found out. Thus, it has been proved that the following polypeptides of the present invention and the DNAs coding the same are novel:

(1). a polypeptide having an amino acid sequence shown in SEQ ID NO. 1

(2) a DNA encoding the polypeptide described above in (1).

(3) a DNA having a nucleotide sequence shown in SEQ ID NO. 2, (4) a DNA having a nucleotide sequence shown in SEQ ID NO. 3

(5) a polypeptide having an amino acid sequence shown in SEQ ID NO. 5, (6) a DNA encoding the polypeptide described above in (5), (7) a DNA having a nucleotide sequence shown in SEQ ID NO. 6, and (8) a DNA having a nucleotide sequence shown in SEQ ID NO. 7.

The present invention is concerned with polypeptides having the amino acid sequence shown in SEQ ID. No. 1 or 5, in substantially purified form, a homologue thereof, or a fragment of the sequence or homologue of a fragment, and DNA encoding such a polypeptide. More particularly, the present invention is related to DNA having the nucleotide sequence shown in SEQ ID No. 2 or 3, and 6 or 7 and DNA having a fragment which is able to selectively hybridize to the nucleotide sequence shown in SEQ ID No. 2 or 3, and 6 or 7.

A polypeptide of Seq. ID No. 1 or 5 in substantially purified form will generally comprise the polypeptide in a preparation in which more than 90%, e.g. 95%, 98% or 99% of the polypeptide in the preparation is that of Seq. ID No. 1 or 5.

A polypeptide homologue of the Seq. ID No. 1 or 5 will be generally at least 70%, preferably at least 80 or 90% and more preferably at least 95% homologous to the polypeptide of Seq. ID No. 1 over a region of at least 20, preferably at least 30, for instance 40, 60 or 80 more, contiguous amino acids. Such polypeptide homologues will be referred to below as a polypeptide according to the invention.

Generally, fragments of Seq. ID No. 1 or 5, or their homologues, will be at least 10, preferably at least 15, for example 20, 25, 30, 40, 50 or 60, amino acids in length, and are also encompassed by the term "a polypeptide according to the invention" as used herein.

A DNA capable of selectively hybridizing to the DNA of Seq. ID No. 2 or 3, and 6 or 7 will be generally at least 70%, preferably at least 80 or 90% and more preferably at least 95%, homologous to the DNA of Seq. ID No. 2 or 3 over a region of at least 20, preferably at least 30, for instance 40, 60 or 100 or more contiguous nucleotides. Such DNA will be encompassed by the term "DNA according to the invention".

Fragments of the DNA of Seq. ID No. 2 or 3, and 6 or 7 will be at least 15, preferably at least 20, for example 25, 30 or 40, nucleotides in length, and are also encompassed by the term "DNA according to the invention" as used herein.

A further embodiment of the invention provides replication and expression vectors comprising DNA according to the invention. The vectors may be, for example, plasmid, virus or phage vectors provided with an origin of replication, optionally a promoter for the expression of said DNA and optionally a regulator of the promoter. The vector may contain one or more selectable marker genes, for example, an anpicillin resistance gene. The vector may be used in vitro, for example in the production of RNA corresponding to the DNA, or used to transfect or transform a host cell.

A further embodiment of the invention provides host cells transformed or transfected with the vectors for the replication and expression of DNA according to the invention, including the DNA SEQ. ID No. 2 or 3, and 6 or 7 or the open reading frame thereof. The cells will be chosen to be compatible with the vector and may, for example, be bacterial, yeast, insect or mammalian cells.

A further embodiment of the invention provides a method of producing a polypeptide which comprises culturing host cells of the present invention under conditions effective to express a polypeptide of the invention. Preferably, in addition, such a method is carried out under conditions in which the polypeptide of the invention is expressed and then produced from the host cells.

DNA according to the invention may also be inserted into the vectors described above in an antisense orientation in order to prove the production of antisense RNA. Antisense RNA may also be produced by synthetic means. Such antisense RNA may be used to control the level of a polypeptide of the invention in a cell.

The invention also provides monoclonal or polyclonal antibodies to a polypeptide according to the invention. The invention further provides a process for the production of monoclonal or polyclonal antibodies to the polypeptides of the invention. Monoclonal antibodies may be prepared by conventional hybridoma technology using a polypeptide of the invention or a fragment thereof, as an immunogen. Polyclonal antibodies may also be prepared by conventional means which comprise inoculating a host animal, for example a rat or a rabbit, with a polypeptide of the invention and recovering immune serum.

The present invention also provides pharmaceutical compositions containing a polypeptide of the invention, or an antibody thereof, in association with a pharmaceutically acceptable diluent and/or carrier.

The polypeptide of the present invention includes polypeptides in which a part of their amino acid sequence is lacking (e.g., a polypeptide comprised of only the essential sequence for revealing a biological activity from an amino acid sequence shown in SEQ ID No. 1 or 5), polypeptides in which a part of their amino acid sequence is replaced by other amino acids (e.g., those replaced by an amino acid having a similar property), and polypeptides in which other amino acids are added or inserted into a part of their amino acid sequence, as well as those having the amino acid sequence shown in SEQ ID NO. 1 or 5.

As is well known, there are one to six codons that encoding one amino acid (for example, it is known that there is one kind of codon for Met, and six codon for leucine (Leu). Accordingly, the nucleotide sequence of DNA can be changed in order to encode a polypeptide having the same amino acid sequence.

The DNA of the present invention, specified in (2) and (6), listed above, includes a group of every nucleotide sequence encoding polypeptides shown in SEQ ID NO. 1 and 5. There is a probability of improving a production yield of a polypeptide by changing a nucleotide sequence.

The DNAs specified in (3) and (7), listed above, are the embodiment of DNAs shown in (2) and (6), and are the natural form of thee sequence.

The DNAs shown in (4) and (8) listed above, indicate the sequence of the DNAs specified in (3) and (7) respectively with a untranslated region.

A signal peptide is a hydrophobic region located immediately downstream of the translation initiation amino acid Met. It is assumed that the signal peptide in the polypeptide of the present invention resides in a region ranging from Met, at the 1-position to Gly at the 21-position, in the amino acid sequence represented by Seq. ID No. 1 or 5. The region essentially responsible for the expression of the biological activity corresponds to the part of the amino acid sequences of the Seq. ID. No. 1 and 5 that lack signal peptides, i.e. the mature protein part. Thus, signal peptides never relate to biological activity.

The DNA having a nucleotide sequence shown in SEQ ID NO. 3 or 7 may be prepared according to the following method:

(i) isolating mRNA from a cell which produces the polypeptide of the present invention (e.g., human pro-B cell line), (ii) preparing a first of cDNA (single strand cDNA) from mRNA obtained as (i) above, followed by preparing a second strand of cDNA (double strand cDNA) (synthesis of cDNA), (iii) inserting cDNA obtained as in (ii) above,into a proper phage vector, (iv) transfecting recombinant phage into host cells (construction of a cDNA library), (v) screening by plaque hybridization, a cDNA library using mouse SDF-1 cDNA as a probe, (vi) preparing phage DNA from a positive clone, followed by cutting out and subcloning the cDNA, and preparing the restriction enzyme map, (vii) determining the nucleotide of sequence each fragment cut by restriction enzymes, followed by assembling the sequence of the full length sequence.

Explained in detail, step (i) may be carried out in accordance with the method of Okayama, et al (described in Enzymology, vol. 154, p3, 1987) after a human pro-B cell line is stimulated by a proper stimulant (e.g. IL-1 etc.) or without stimulation.

An example of the cell which secretes the polypeptides of the present invention is preferably the human pro-B cell line FLEB14. Human cell line FLEB14 may be supplied by 1st lecture, Medicinal Chemistry, School of Medicine, Kyoto University.

Steps (ii), (iii) and (iv) are a series of steps for preparing a cDNA library, and may be carried out in accordance with the method of Glubler & Hoffman (Gene, vol. 25, pp. 263, 1983) with a slight modification.

As examples of the vector used in the step (iii), many plasmid vectors (e.g. pB322, pBluescript etc.), and phage vectors (e.g.λgt10,λDASH II etc.) are known, and phage vector λgt10 (43.3 kbp, Stratagene) is preferable.

The host cell used in step (iv) is preferably *E. coli* NM514 (Stratagene).

Steps (v) and (vi) may be carried out in accordance with the method described in Molecular Cloning (written by Sam Brook, Fritsh, E. F. and Maniatis, T., published by Cold Spring Harbor Laboratory Press in 1989.).

DNA sequencing according to step (vii) may be carried out in accordance with the method of Maxam-Gilbert or the dideoxy termination method.

It is necessary to confirm that the cDNA obtained covers a complete or almost complete length of intact mRNA. This confirmation may be carried out by Northern analysis using the cDNA as a probe (see Molecular Cloning).

If the size of the mRNA obtained from the hybridized band and the size of the cDNA are almost same, the cDNA is considered to be almost full length.

Once the nucleotide sequences shown in SEQ ID NOs. 2, 3, 6, 7 are determined, DNA of the present invention may be obtained by chemical synthesis, by the PCR method, or by hybridization making use of a fragment of DNA of the present invention, as a probe. Furthermore, DNA of the present invention may be obtained in a desired amount by transforming a proper host with a vector that contains DNA according to the present invention, followed by culturing the transformant.

The polypeptides of the present invention (shown in SEQ ID NO. 1 or 5) may be prepared by:

(1) isolating and purifying such polypeptides from an organism or a cultured cell, (2) chemical synthesis, or (3) using a skill of biotechnology, preferably, by the method described in (3).

Examples of the expression system that may be used when preparing a polypeptide by using a skill of biotechnology, are, for example, the expression systems of bacteria, yeast, insect cells and mammalian cells.

For example, the expression in *E. coli* may be carried out by adding the initiation codon (ATG) to 5' end of a DNA encoding the mature protein, connecting the DNA thus obtained downstream of a proper promoter (e.g., trp promoter, lac promoter, IPL promoter, and T7 promoter), and then inserting it into a vector (e.g., pBR322, and pUC18, and pUC19) which functions in an *E. coli* strain to prepare an expression vector.

When a bacterial signal peptide (e.g., signal peptide of pel B) is utilized, the desired polypeptide may also be produced in periplasm. Furthermore, a fusion protein with another polypeptide may also be easily produced.

Furthermore, expression in a mammalian cell may be carried out, for example, by inserting the DNA shown in SEQ ID NO. 3 or 6 downstream of a proper promoter (e.g., SV40 promoter, LTR promoter, and metallothionein promoter) in a proper vector (e.g., retrovirus vector, papilloma virus vector, vacciniavirus vector, and SV40 vector.) to obtain an expression vector, and transfecting a proper mammalian cell (e.g., monkey COS-7 cell, Chinese hamster CHO cell, and mouse L cell) with the expression vector thus obtained, and then culturing the transformant in a proper medium to get the desired polypeptide in the culture medium. The polypeptide thus obtained may be isolated and purified by conventional biochemical methods.

Effects of the Invention

Polypeptides of the present invention are produced and secreted in pro-B cells, so they may be used for diseases relating to undergrown or abnormal proliferation of hematopoietic cells, neuronal enhancement or depression, immunological enhancement and depression; for example, inflammatory diseases (rheumatoid arthritis, ulcerative colitis), hematopoietic stemcytopenia after bone marrow transplantation, leukocytopenia, thrombocytopenia, B lymphopenia and T lymphopenia after chemotherapy, anemia, infectious diseases, cancer, leukocytosis, AIDS, neurodegenerative diseases (Alzheimer, multiple sclerosis), prevention or treatment of neuronal injury, prevention or treatment of disorders of bone metabolism (osteoporosis) or tissue repair.

In regard to the above activities, it was confirmed that the mouse SDF-1α stimulated the proliferation of the mouse myeloid progenitor cell line DA1G in the laboratory test. It was suggested that human SDF-1α also has the same activity.

Further, polyclonal or monoclonal antibodies against the polypeptide of the present invention can be used in the determination of the amount of said polypeptide in the organism, and thereby, may be utilized for the purpose of investigating the relationship between the polypeptide and diseases, or for the purpose of diagnosing diseases. Polyclonal and monoclonal antibodies may be prepared by conventional methods by using the said polypeptide or the fragment thereof as an antigen.

The DNA of the present invention may be utilized as an important and essential template in preparing the polypeptide of the present invention, which is expected to for the diagnosis of and treatment of genetic diseases (the treatment of gene defect diseases by inhibiting expression of the polypeptide by antisense DNA (RNA)). Further, genomic DNA may be isolated by using the DNA of the present invention as a probe. Similarly, it is possible to isolate genes having high homology to the DNA of the present invention in humans or other species.

Application for Pharmaceuticals

The polypeptides of the present invention are produced and secreted in pro-B cells, so they may be used for diseases relating to undergrown or abnormal proliferation of hematopoietic cells, neuronal enhancement or depression, immunological enhancement and depression; for example, inflammatory diseases (rheumatoid arthritis, ulcerative colitis), hematopoietic stemcytopenia after bone marrow transplantation, leukocytopenia, thrombocytopenia, B lymphopenia and T lymphopenia after chemotherapy, anemia, infectious diseases, cancer, leukocytosis, AIDS, neurodegenerative diseases (Alzheimer, multiple sclerosis), prevention or treatment of neuronal injury, prevention or treatment of disorders of bone metabolism (osteoporosis) or tissue repair.

The polypeptides of the present invention may be administered systemically or partially, usually by oral or parenteral administration; preferably by orally, intravenously or intraventricularly administration.

The doses to be administered are determined depending upon age, body weight, symptom, the desired therapeutic effect, the route of administration, and the duration of the treatment. In the human adult, doses per person per dose are generally between 100 µg and 100 mg, by oral administration, up to several times per day; and between 10 µg and 100 mg, by parenteral administration, up to several times per day.

As mentioned above, the doses to be used depend upon various conditions. Therefore, there are cases in which doses lower than or greater than the ranges specified above may be used.

Administration of the compounds of the present invention, may be as solid compositions, liquid compositions or other compositions for oral administration; as injections, liniments or suppositories for parenteral administration.

Solid compositions for oral administration include compressed tablets, pills, capsules, dispersible powders, and granules. Capsules include soft capsules and hard capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, or magnesium metasilicate aluminate,). The compositions may also comprise, additional substances other than inert diluents e.g. lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid etc.)).

The tablets or pills may, if desired, be coated with a film of gastric or enteric material (such as sugar, gelatin, hydroxypropyl cellulose or hydroxypropylmethyl cellulose phthalate), or be coated with more than two films. And further, the coating may be containment within capsules of absorbable materials, such as gelatin.

Other compositions for oral administration included spray compositions which may be prepared by known methods and which comprise one or more of the active compound(s). Spray compositions may comprise additional substances other than inert diluents, e.g. stabilizing agents (sodium sulfite), and isotonic buffers (sodium chloride, sodium citrate, citric acid). For preparation of such spray compositions, for example, the method described in the U.S. Pat. No. 2,868,691 or 3,095,355 (herein incorporate by reference) may be used.

Injections may comprise additional substances other than inert diluents; e.g. preserving agents, wetting agents, emulsifying agents, dispersing agents, stabilizing agent (such as human serum albumin, lactose), and assisting agents such as assisting agents for dissolving (arginine, asparaginic acid).

These substances may be sterilized, for example, by filtration through a bacteria-retaining filter, by incorporation of sterilizing agents in the compositions or by irradiation. They may also be manufactured in the form of sterile solid compositions, for example, by freeze-drying, and which can be dissolved in sterile water or some other sterile diluents for injection immediately before used.

Other compositions for parenteral administration include liquids for external use, endermic liniments (ointment), suppositories for rectal administration and pessaries, which comprise one or more of the active compound(s) and may be prepared by known methods.

EXAMPLE

The following examples illustrates, but do not limit, the present invention.

Example 1: Northern analysis of human cell line FLEB14

Human pro-B cell line FLEB14 cells (See Katamine, S., et al. Nature, 309, 369 (1984)) were homogenated. The homogenate was incubated with oligo-dT cellulose. Poly(A) RNA was eluted after washing (Vennstorm, B. et al Cell,28, 135(1982)). 1 μg of poly(A) RNA was electrophoresed in a 1.0% agarose gel and then blotted to a nitrocellulose membrane.

The membrane was hybridized with the 32P-labeled mouse SDF-1 (described as seq. ID No. 3 in Japanese Patent Application No. 5-22098; the sequence is shown in seq. ID No. 9.; the factor is now called SDF-1 α, as another SDF-1 was found from mouse.)) cDNA with 50% formamide, 5×SSC, 0.1% SDC, 0.1% SDS, 5×Denhaldt's, 0.1 mg/ml Salmon sperm DNA at 39° C. and washed with 0.3M NaCl, 30 mM Na citrate, 0.1 % SDS at 50° C. and then autoradiogramed. 3.5 kb and 1.9 kb mRNA hybridized.

Example 2: preparation of cDNA from mRNA of human pro-B cell line

A cDNA library was constructed from human pro-B cell line FLEB14 cells by the conventional method (See Molecular Cloning ; Sambrook, J., Fritsh, E. F., & Maniatis, T, Cold Spring Harbor Laboratory Press (1989)). cDNA was synthesized using Time Saver cDNA synthesis kit (Pharmacia).

The first strand was synthesized from FLEB14 poly(A)-RNA (5 μg) using a reverse transcriptase and an oligo-dT primer. The double strand cDNA was synthesized using DNA polymerase 1.

cDNA was ligated with an EcoRl-NotI adapter:

AATTCGCGGCCGCT (SEQ ID NO. 10)

GCGCCGGCGAp (SEQ ID NO. 11)

and then phosphorylated, cDNA larger than 800 bp were recovered from a 0.8% agarose gel with a glass powder (Geneclean II DNA purification kit, available from Biol101).

Example 3: Preparation of cDNA library and cross hybridization

The cDNA obtained in Example 2 was ligated into a λgt10 phase vector (available from Stratagene) which have EcoRI arm treated with phosphatase.

In vitro packaging followed the protocol of the in vitro packaging kit LAMDA INN (available from Nihon gene). The recombinant phages were transfected to host E. Coli NM514 (available from Stratagene). A cDNA library containing 1×10 6 plaques was obtained. 1×10 6 λgt10 phage plaques of the cDNA library were transfected to nitrocellulose membranes. The membranes were hybridized with 32P-labeled mouse SDF-1α cDNA (shown in seq. ID No. 9, the same cDNA used in Example 1) in 50% formamide, 5×SSD, 0.1% SDS, 5× Denhaldt's 0.1 mg/ml Salmon sperm DNA, at 39° C. and washed in 0.3M NaCl, 30 mM Na citrate, 0.1% SDS at 50° C. and autoradiogramed. 40 positive clones were obtained.

Example 4: Isolation of positive clones

Phage DNA was prepared from 9 positive clones by the conventional method (See Cell Technology Experimental Protocol, pp. 8, published by Shuujun-sha). Phage DNA was digested with Not I. The length of the inserted cDNA were measured by agarose gel electrophoresis. 8 clones were 1.9 kb long, and the length of one clone was 3.5 kb long. It was thought that these two types of clones are almost full length human SDF-1α and SDF-β cDNA from the result of Northern analysis.

cDNA from one clone 1.9 kb in length, and from one clone 3.5 kb in length were digested with at Not I, were subjected to agarose electrophoresis, and the fragments were cut out and then subcloned at the Not I site of plasmid pBluescript.

Example 5: Preparation of restriction enzyme map and sequencing

Figure 1:
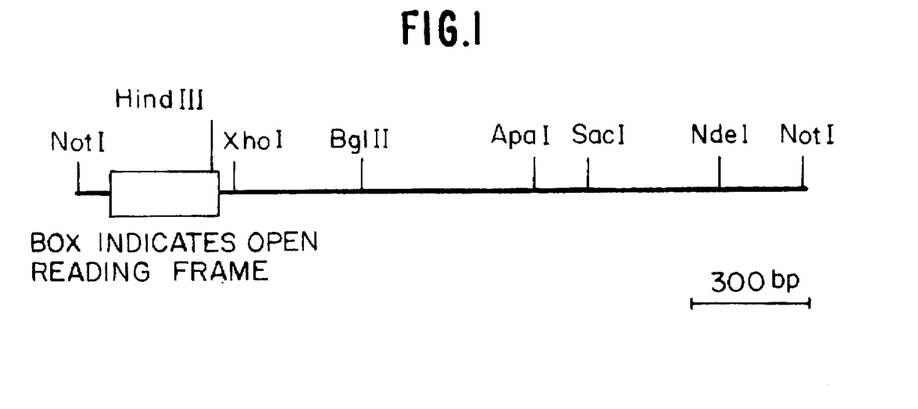
FIG. 1 is the restriction enzyme map of the cDNA clone (1.9 kb) of SDF-1 α.

A restriction enzyme map of human SDF-1 (1.9 kb) was prepared (shown in FIG. 1). Nucleobide sequences of about 300 bp from both ends of each restriction fragment where determined. Upon assembing these sequences, the full length nucleotide sequences were determined (shown in Seq. ID. No. 3).

An open reading frame and an amino acid sequence were determined from the nucleotide sequence of the full length cDNA, with the results shown in Seq. ID No. 1. 30–40 amino acids of the N-termini obtained was compared with known signal peptide, and a signal peptide of the polypeptides of the present invention was presumed (sequence shown in seq. ID No. 4)(See Von Heuane, G. Nucleic Acids Res. 14 ,4683 (1986)).

Figure 2:
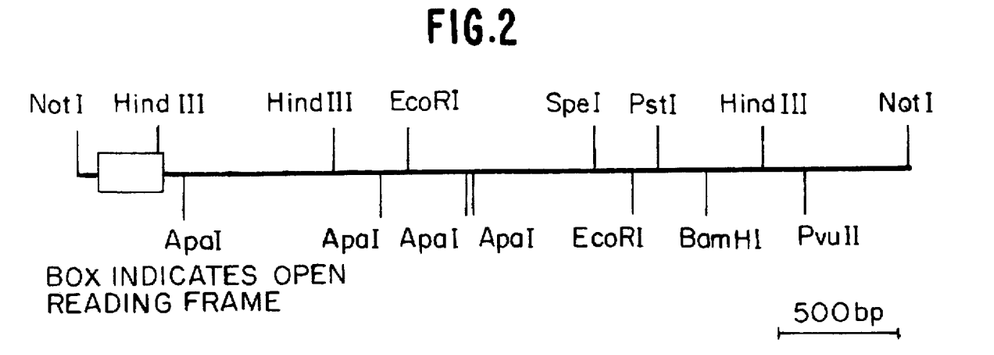
FIG. 2 is the restriction enzyme map of the cDNA clone (3.5 kb) of SDF-1 β.

By the same procedure as described above, a restriction enzyme map (shown in FIG. 2), full length nucleotide sequences (shown in seq. ID No. 7), an open reading frame (shown in seq. ID No. 6), an amino acid sequence (shown in seq. ID No. 5) and a signal peptide sequence (shown in seq. ID No. 8) of the 3.5 kb clone were obtained.

The deduced amino acid sequences of the 3.5 kb clone and the 1.9 kb clone were very similar each other, so the 1.9 kb clone was named SDF-1α and the 3.5 kb clone was named SDF-1β.

The Nucleotide sequences were determined by the cycle sequence method using a fluorescence determinator (supplied by Applied Biosystem Inc.). Nucleotide sequences were read by a DNA sequencer (Model 373, supplied by Applied Biosystem Inc.).

The nucleotide sequences and the deduced amino acid sequences of SDF-1α and 1β were homology searched in a computer data base (GENBANK and EMBL for DNA, NBRF and SWISSPROT for amino acid sequence). It was confirmed that cDNAs of the present invention encode novel peptides.

Example 6: Construction of plasmid vector for use in the preparation of a expression vector As an expression vector, a pUC-SRαML-1 (preparation of which is disclosed in European Patent publication No. 559428) derivative was used. This derivative was constructed so as to insert two fragments, as shown below:

fragment T7 5' GTAATACGACTCACTATAGGG-GAGAGCT 3' (SEQ ID NO. 12)

3' ACGTCATTATGCTGAGTGATATCCCCTC 5' (SEQ ID NO. 13)

between the PstI and SacI sites and fragment SP6 5' CTAGTCTATAGTGTC CCTAAATCGTGGGTAC 3' (SEQ ID NO. 14)

3' AGATATCACAGTGGATmTAGGAC 5' (SEQ ID NO. 15)

between the SpeI and KpnI sites in the multi-cloning site, respectively.

Figure 3:
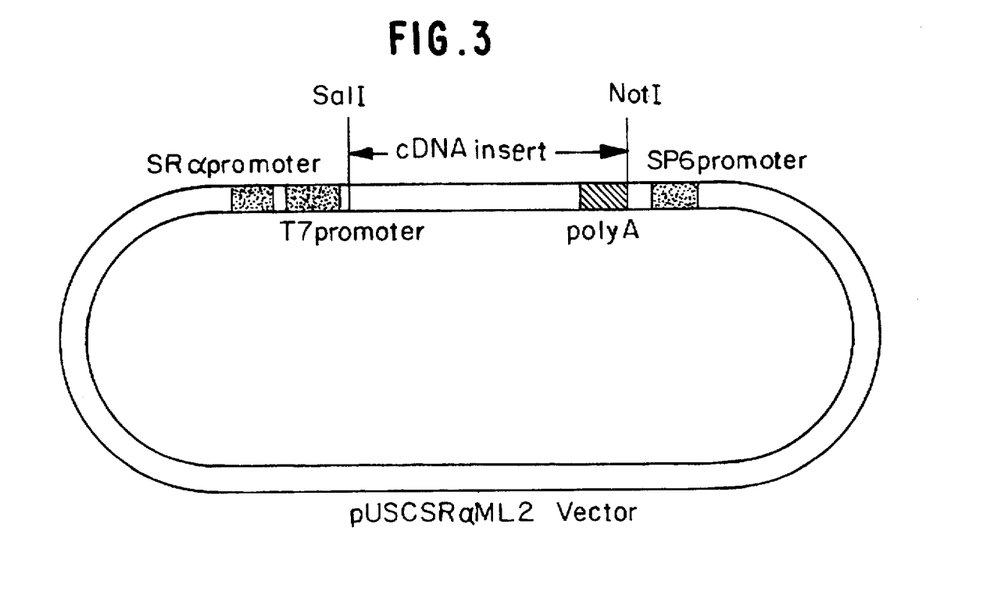
FIG. 3 is the map of the plasmid vector pUC-SR αML2.

The pUC-SRαML1 vector was digested with PstI and SacI and the resulting digest was subjected to agarose gel electrophoresis to prepare and recover about a 4.1 kbp fragment and thereafter the 5'-end phosphoric acid group was removed by BAP (bacterial alkaline phosphatase) treatment. The phosphorylated DNA fragment T7 was ligated with the thus prepared about 4.1 kbp fragment from pUC-SRαML1 to make a circular form. The resulting vector was, then digested with SpeI and KpnI and the resulting digest was subjected to agarose gel electrophoresis to prepare and recover an about 4.1 kbp fragment and thereafter the 5'-end phosphoric acid group was removed by BAP (bacterial alkaline phosphatase) treatment. The phosphorylated DNA fragment SP6 was ligated with the thus prepared about 4.1 kbp fragment to make a circular form. The plasmid vector constructed in this manner was named pUC-SRαML2 (See FIG. 3).

Example 7: Construction of expression vector

Regarding hSDF-1 α, primer X, Y and YH were synthesized. The sequence of primer X, Y and YH are as follows:

Primer X 5'-A ATA TAG TCG ACC ACC ATG AAC GCC AAG GTC GTG GTC GTG CTG G-3' (SEQ ID NO. 16)

Primer Y 5'-CGG CGG ACT AGT TTA CrT GTT TAA AGC TTT CTC CAG G-3' (SEQ ID NO. 17)

Primer YH 5'-GCC GCC ACT AGT TTA GTG GTG GTG GTG GTG GTG CTT GTT TAA AGC TTT CTC CAG -3' (SEQ ID NO. 18)

The hSDF-1 α plasmid was subjected to PCR using the thus synthesized oligonucleotides X and Y as primers. The thus obtained PCR fragment contains a sequence placed 5'-adjacent to the initiation codon, that corresponds to the Kozac sequence which is known among those skilled in the art, and cDNA which encodes a protein molecule consisting of the hSDF-1α protein. The PCR fragment was digested with SalI and SpeI and the resulting digest was separated and purified and then inserted into the SalI - SpeI site of pUC-SRαML2 prepared in example 6, to obtain the expression vector pUC-SRαML2 -hSDF-1αA.

Moreover, the hSDF-1α plasmid was subjected to PCR using the synthesized oligonucleotides X and YH as primers. The thus obtained PCR fragment contains a sequence placed 5'-adjacent to the initiation codon, that corresponds to Kozac sequence which is known among those skilled in the art, and cDNA which encodes a protein molecule consisting of the hSDF-1α protein and six additional histidine (His) residues attached to its C-terminal end. The PCR fragment was digested with SalI and SpeI and the resulting digest was separated and purified and then inserted into the SalI - SpeI site of pUC-SRαML2 prepared in example 6, to obtain the expression vector pUC-SRcαML2-hSDF-1αB.

As for hSDF-1 β, primer Z and ZH were synthesized. Sequences of primer Z and ZH are as follows:

Primer Z 5'-GG CGG ACT AGT TCA CAT CTT GAA CCT CTT GTT TAA AGC -3' (SEQ ID NO. 19)

Primer ZH 5'-GCC GCC ACT AGT TCA GTG GTG GTG GTG GTG GIG CAT CTT GAA CCT CTT GTT TAA AM -3' (SEQ ID NO. 20)

The hSDF-1 β plasmid was subjected to PCR using the thus synthesized oligonucleotides X and Z as primers. The thus obtained PCR fragment contains a sequence placed 5'-adjacent to the initiation codon, that corresponds to the Kozac sequence which is known among those skilled in the art, and cDNA which encodes a protein molecule consisting of the hSDF-1β protein. The PCR fragment was digested with SalI and SpeI and the resulting digest was separated and purified and then inserted into the SalI - SpeI site of pUC-SRαML2 prepared in example 6 to obtain the expression vector pUC-SRαML2-hSDF-1 βA.

Moreover, the hSDF-1β plasmid was subjected to PCR using the synthesized oligonucleotides X and ZH as primers. The thus obtained PCR fragment contains a sequence placed 5'-adjacent to the initiation codon, that corresponds to the Kozac sequence which is known among those skilled in the art, and cDNA which encodes a protein molecule consisting of the hSDF-1β protein and six additional histidine (His) residues attached to its C-terminal end. The PCR fragment was digested with SalI and SpeI and the resulting digest was separated and purified and then inserted into the SalI - SpeI site of pUC-SRαML2 prepared in example 6, to obtain the expression vector pUC-SRαML2 -hSDF-1βB.

Each of the thus constructed pUC-SRαML2-hSDF-1 αA, pUC-SRαML2-hSDF-1αB, pUC-SRαML2-hSDF-1βA and pUC-SRαML2-hSDF-1β plasmids were transfected into *E. coli* strain DH5, recovered from a 100 ml culture of the resulting transformant and then purified by CsCl density gradient centrifugation twice.

Example 8: Expression in COS cells

Each of the plasmid DNA preparations pUC-SRαML2, pUC-SRαML2-hSDF-1 αA, pUC-SRαML2-hSDF-1αB, pUC-SRαML2-hSDF-1βA and pUC-SRαaML2-hSDF-1βB were introduced into COS-7 cells (Cell, vol. 23, p. 175, 1981) by means of the diethylaminoethyl (DEAE) dextran method (J. Immunology, vol. 136, p. 4291, 1986).

That is, about $1.8 \times 10^6$ COS-7 cells were inoculated into a 225 cm$^2$ capacity flask (manufactured by Corning) together with 50 ml of a liquid culture medium (Dulbecco's modified MEM medium supplemented with 10% decomplemented fetal bovine serum). After overnight incubation in a carbon dioxide incubator (37° C., 5% CO2) and subsequent removal of the culture supernatant, 12 ml of a DNA cocktail (Dulbecco's modified MEM medium supplemented with 15 µg of each plasmid DNA, 50 mM Tris-HCl buffer (pH 7.4) and 400 µg/ml of DEAE-dextran) was added to each flask and culturing was carried out for 3 hours at 37° C. in an atmosphere of 5% CO2. Thereafter, the DNA cocktail was replaced by 15 ml of a chloroquine solution (Dulbecco's modified MEM medium supplemented with 150 µM chloroquine and 7% decomplemented fetal bovine serum), followed by additional 3 hours of culturing.

After removing the chloroquine solution, the aforementioned liquid culture medium (50 ml) was added to each of the resulting flasks which were then incubated at 37° C. in an atmosphere of 5% CO2 for 72 hours until growth of the cells in each flask almost forms a monolayer. After removing the culture supernatant, the cells in each flask were washed with a serum-free liquid culture medium (trade name, SFM-101; available from Nissui Pharmaceutical Co., Ltd.) and then supplied with 75 ml of the same serum-free liquid culture medium, and the culturing was continued for another 72 hours. Thereafter, the resulting culture supernatant was recovered and filtered through a membrane filter (trade name, STERIVEX-GS; available from Millipore Corp.) to remove the cells and cell debris. The thus obtained culture supernatant samples were stored at 4° C. for future use. A culture supernatant of COS cells which have been transformed with plasmid containing the hSDF-1α and β cDNA inserts are expected to contain expressed and secreted mature protein moieties of polypeptides which correspond to hSDF-1α and β.

Example 9: Confirmation of expression

A 2 ml portion of each of the culture supernatants of transformed COS cells obtained in Example 8 was concentrated to a volume of 100 ml using a centrifugal concentration filter (trade name, Centricon-10; available from Millipore Corp.). A 1 μl portion of each of the thus concentrated samples was mixed with the same volume of a loading buffer (0.125M Tris-HCI buffer (pH 6.8), 4% sodium dodecyl sulfate and 30% glycerol) for SDS-PAGE (sodium dodecyl sulfate polyacrylamide gel electrophoresis) use, and the mixture was treated at 90° C. for 3 minutes and then subjected to SDS-PAGE.

In the case of the hSDF-1αB and βB proteins having the His hexamer introduced to the C-terminus of the proteins, not only their corresponding COS cell culture supernatant but also their purified products were subjected to SDS-PAGE analysis.

Purification of the protein was carried out by means of metal chelate affinity chromatography (Biotechnology, vol. 9, p. 273, 1991), making use of the function of His to form complex compounds with various transition metal ions. That is, a culture supernatant (350 ml) obtained from COS cells was mixed with a sodium chloride aqueous solution in such an amount that the final concentration of the salt became 1M, and the resulting mixture was applied to a column packed with 4 ml of a zinc-linked chelating Sepharose (trade name, Chelating Sepharose Fast-Flow; available from Pharmacia) to adsorb the protein to the resin. The column was washed with 50 mM phosphate buffer (pH 7.0) containing 1M sodium chloride aqueous solution (40 ml), and the protein retained in the column was eluted with 50 mM phosphate buffer (pH 7.0) containing 1M sodium chloride aqueous solution and 0.4M imidazole. Thereafter, the resulting elute was concentrated to a volume of 100 μl, and a portion of the concentrated sample was subjected to SDS-PAGE analysis. The SDS-PAGE analysis was carried out using a SDS 10/20 gradient gel and a product which corresponds to a molecular weight of hSDF-1α and SDF-1β was detected, respectively.

What is claimed is:

1. A substantially pure stromal derived factor-1α (SDF-1α) polypeptide having the amino acid sequence as shown in SEQ ID NO:1.

2. A composition comprising the polypeptide of claim 1; and a pharmaceutically acceptable carrier or diluent.

3. A substantially pure stromal derived factor-1β (SDF-1β) polypeptide having the amino acid sequence as shown in SEQ ID NO:5.

4. A composition comprising the polypeptide of claim 3; and a pharmaceutically acceptable carrier or diluent.

5. An isolated stromal derived factor-1α (SDF-1α) polypeptide having the amino acid sequence as shown in SEQ ID NO:1.

6. An isolated stromal derived factor-1β (SDF-1β) polypeptide having the amino acid sequence as shown in SEQ ID NO:5.

7. A substantially pure mature polypeptide of stromal derived factor-1α (SDF-1α) polypeptide having the amino acid sequence from Lys at position 22 to Lys at position 89 shown in SEQ ID NO:1.

8. A substantially pure mature polypeptide of stromal derived factor-1β (SDF-1β) polypeptide having the amino acid sequence from Lys at position 22 to Met at position 93 shown in SEQ ID NO:5.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
  ( A ) LENGTH: 89 amino acids
  ( B ) TYPE: amino acid
  ( D ) TOPOLOGY: linear ( i i ) MOLECULE TYPE: protein ( x i ) SEQUENCE DESCRIPTION: SEQ ID NO:1:

| Met | Asn | Ala | Lys | Val | Val | Val | Leu | Val | Leu | Val | Leu | Thr | Ala | Leu |
|---|---|---|---|---|---|---|---|---|---|---|---|---|---|---|
| 1 | | | | 5 | | | | | 10 | | | | | 15 |
| Cys | Leu | Ser | Asp | Gly | Lys | Pro | Val | Ser | Leu | Ser | Tyr | Arg | Cys | Pro | Cys |
| | | | 20 | | | | | 25 | | | | | 30 | | |
| Arg | Phe | Phe | Glu | Ser | His | Val | Ala | Arg | Ala | Asn | Val | Lys | His | Leu | Lys |
| | | 35 | | | | | 40 | | | | | 45 | | | |
| Ile | Leu | Asn | Thr | Pro | Asn | Cys | Ala | Leu | Gln | Ile | Val | Ala | Arg | Leu | Lys |
| | 50 | | | | | 55 | | | | | 60 | | | | |
| Asn | Asn | Asn | Arg | Gln | Val | Cys | Ile | Asp | Pro | Lys | Leu | Lys | Trp | Ile | Gln |
| 65 | | | | | 70 | | | | | 75 | | | | | 80 |
| Glu | Tyr | Leu | Glu | Lys | Ala | Leu | Asn | Lys |
| | | | | 85 | | | | |

( 2 ) INFORMATION FOR SEQ ID NO:2:

( i ) SEQUENCE CHARACTERISTICS:
  ( A ) LENGTH: 267 base pairs
  ( B ) TYPE: nucleic acid
  ( C ) STRANDEDNESS: single
  ( D ) TOPOLOGY: linear ( i i ) MOLECULE TYPE: cDNA to mRNA ( x i ) SEQUENCE DESCRIPTION: SEQ ID NO:2:

| | | | | | |
|---|---|---|---|---|---|
| ATGAACGCCA | AGGTCGTGGT | CGTGCTGGTC | CTCGTGCTGA | CCGCGCTCTG | CCTCAGCGAC | 60 |
| GGGAAGCCCG | TCAGCCTGAG | CTACAGATGC | CCATGCCGAT | TCTTCGAAAG | CCATGTTGCC | 120 |
| AGAGCCAACG | TCAAGCATCT | CAAAATTCTC | AACACTCCAA | ACTGTGCCCT | TCAGATTGTA | 180 |
| GCCCGGCTGA | AGAACAACAA | CAGACAAGTG | TGCATTGACC | CGAAGCTAAA | GTGGATTCAG | 240 |
| GAGTACCTGG | AGAAAGCTTT | AAACAAG | | | | 267 |

( 2 ) INFORMATION FOR SEQ ID NO:3:

( i ) SEQUENCE CHARACTERISTICS:
        ( A ) LENGTH: 1856 base pairs
        ( B ) TYPE: nucleic acid
        ( C ) STRANDEDNESS: single
        ( D ) TOPOLOGY: linear     ( i i ) MOLECULE TYPE: cDNA to mRNA     ( x i ) SEQUENCE DESCRIPTION: SEQ ID NO:3:

| | | | | | |
|---|---|---|---|---|---|
| TCTCCGTCAG | CCGCATTGCC | CGCTCGGCGT | CCGGCCCCCG | ACCCGTGCTC | GTCCGCCCGC | 60 |
| CCGCCCGCCC | GCCCGCGCCA | TGAACGCCAA | GGTCGTGGTC | GTGCTGGTCC | TCGTGCTGAC | 120 |
| CGCGCTCTGC | CTCAGCGACG | GGAAGCCCGT | CAGCCTGAGC | TACAGATGCC | CATGCCGATT | 180 |
| CTTCGAAAGC | CATGTTGCCA | GAGCCAACGT | CAAGCATCTC | AAAATTCTCA | ACACTCCAAA | 240 |
| CTGTGCCCTT | CAGATTGTAG | CCCGGCTGAA | GAACAACAAC | AGACAAGTGT | GCATTGACCC | 300 |
| GAAGCTAAAG | TGGATTCAGG | AGTACCTGGA | GAAAGCTTTA | AACAAGTAAG | CACAACAGCC | 360 |
| AAAAAGGACT | TTCCGCTAGA | CCCACTCGAG | GAAAACTAAA | ACCTTGTGAG | AGATGAAAGG | 420 |
| GCAAAGACGT | GGGGGAGGGG | GCCTTAACCA | TGAGGACCAG | GTGTGTGTGT | GGGGTGGGCA | 480 |
| CATTGATCTG | GGATCGGGCC | TGAGGTTTGC | AGCATTTAGA | CCCTGCATTT | ATAGCATACG | 540 |
| GTATGATATT | GCAGCTTATA | TTCATCCATG | CCCTGTACCT | GTGCACGTTG | AACTTTTAT | 600 |
| TACTGGGGTT | TTTCTAAGAA | AGAAATTGTA | TTATCAACAG | CATTTCAAG | CAGTTAGTTC | 660 |
| CTTCATGATC | ATCACAATCA | TCATCATTCT | CATTCTCATT | TTTAAATCA | ACGAGTACTT | 720 |
| CAAGATCTGA | ATTTGGCTTG | TTTGGAGCAT | CTCCTCTGCT | CCCCTGGGGA | GTCTGGGCAC | 780 |
| AGTCAGGTGG | TGGCTTAACA | GGGAGCTGGA | AAAAGTGTCC | TTTCTTCAGA | CACTGAGGCT | 840 |
| CCCGCAGCAG | CGCCCCTCCC | AAGAGGAAGG | CCTCTGTGGC | ACTCAGATAC | CGACTGGGGC | 900 |
| TGGGGCGCCG | CCACTGCCTT | CACCTCCTCT | TTCAAACCTC | AGTGATTGGC | TCTGTGGGCT | 960 |
| CCATGTAGAA | GCCACTATTA | CTGGGACTGT | CTCAGAGACC | CCTCTCCCAG | CTATTCCTAC | 1020 |
| TCTCTCCCCG | ACTCCGAGAG | CATGCTTAAT | CTTGCTTCTG | CTTCTCATTT | CTGTAGCCTG | 1080 |
| ATCAGCGCCG | CACCAGCCGG | GAAGAGGGTG | ATTGCTGGGG | CTCGTGCCCT | GCATCCCTCT | 1140 |
| CCTCCCAGGG | CCTGCCCAC | AGCTCGGGCC | CTCTGTGAGA | TCCGTCTTTG | GCCTCCTCCA | 1200 |
| GAATGGAGCT | GGCCCTCTCC | TGGGGATGTG | TAATGGTCCC | CCTGCTTACC | GGCAAAAGAC | 1260 |
| AAGTCTTTAC | AGAATCAAAT | GCAATTTTAA | ATCTGAGAGC | TCGCTTGAGT | GACTGGGTTT | 1320 |
| GTGATTGCCT | CTGAAGCCTA | TGTATGCCAT | GGAGGCACTA | ACAAACTCTG | AGGTTTCCGA | 1380 |
| AATCAGAAGC | GAAAAAATCA | GTGAATAAAC | CATCATCTTG | CCACTACCCC | CTCCTGAAGC | 1440 |
| CACAGCAGGG | GTTCAGGTTC | CAATCAGAAC | TGTTGGCAAG | GTGACATTTC | CATGCATAGA | 1500 |
| TGCGATCCAC | AGAAGGTCCT | GGTGGTATTT | GTAACTTTTT | GCAAGGCATT | TTTTTATATA | 1560 |
| TATTTTTGTG | CACATTTTTT | TTTACGATTC | TTTAGAAAAC | AAATGTATTT | CAAAATATAT | 1620 |

```
TTATAGTCGA ACAAGTCATA TATATGAATG AGAGCCATAT GAATGTCAGT AGTTTATACT        1680

TCTCTATTAT CTCAAACTAC TGGCAATTTG TAAAGAAATA TATATGATAT ATAAATGTGA        1740

TTGCAGCTTT TCAATGTTAG CCACAGTGTA TTTTTCACT  TGTACTAAAA TTGTATCAAA        1800

TGTGACATTA TATGCACTAG CAATAAAATG CTAATTGTTT CATGGTAAAA AAAAAA           1856
```

( 2 ) INFORMATION FOR SEQ ID NO:4:

( i ) SEQUENCE CHARACTERISTICS:
        ( A ) LENGTH: 1856 base pairs
        ( B ) TYPE: nucleic acid
        ( C ) STRANDEDNESS: single
        ( D ) TOPOLOGY: linear     ( i i ) MOLECULE TYPE: cDNA to mRNA     ( v i ) ORIGINAL SOURCE:
        ( A ) ORGANISM: Homo sapiens
        ( H ) CELL LINE: FLEB14

( i x ) FEATURE:
        ( A ) NAME/KEY: CDS
        ( B ) LOCATION: 80..349
        ( C ) IDENTIFICATION METHOD: by similarity to some other pattern     ( i x ) FEATURE:
        ( A ) NAME/KEY: sig_peptide
        ( B ) LOCATION: 80..142
        ( C ) IDENTIFICATION METHOD: by similarity with known sequence
            or to an established consensus     ( i x ) FEATURE:
        ( A ) NAME/KEY: mat_peptide
        ( B ) LOCATION: 143..346
        ( C ) IDENTIFICATION METHOD: by similarity with known sequence
            or to an established consensus     ( x i ) SEQUENCE DESCRIPTION: SEQ ID NO:4:

```
TCTCCGTCAG CCGCATTGCC CGCTCGGCGT CCGGCCCCCG ACCCGTGCTC GTCCGCCCGC         60

CCGCCCGCCC GCCCGCGCC ATG AAC GCC AAG GTC GTG GTC GTG CTG GTC CTC        112
                    Met Asn Ala Lys Val Val Val Val Leu Val Leu
                    -21 -20                    -15

GTG CTG ACC GCG CTC TGC CTC AGC GAC GGG AAG CCC GTC AGC CTG AGC         160
Val Leu Thr Ala Leu Cys Leu Ser Asp Gly Lys Pro Val Ser Leu Ser
-10              -5                  1                   5

TAC AGA TGC CCA TGC CGA TTC TTC GAA AGC CAT GTT GCC AGA GCC AAC         208
Tyr Arg Cys Pro Cys Arg Phe Phe Glu Ser His Val Ala Arg Ala Asn
             10                  15                  20

GTC AAG CAT CTC AAA ATT CTC AAC ACT CCA AAC TGT GCC CTT CAG ATT         256
Val Lys His Leu Lys Ile Leu Asn Thr Pro Asn Cys Ala Leu Gln Ile
         25                  30                  35

GTA GCC CGG CTG AAG AAC AAC AAC AGA CAA GTG TGC ATT GAC CCG AAG         304
Val Ala Arg Leu Lys Asn Asn Asn Arg Gln Val Cys Ile Asp Pro Lys
     40                  45                  50

CTA AAG TGG ATT CAG GAG TAC CTG GAG AAA GCT TTA AAC AAG TAAGCACAAC      356
Leu Lys Trp Ile Gln Glu Tyr Leu Glu Lys Ala Leu Asn Lys
 55                  60                  65

AGCCAAAAAG GACTTTCCGC TAGACCCACT CGAGGAAAAC TAAAACCTTG TGAGAGATGA        416

AAGGGCAAAG ACGTGGGGGA GGGGGCCTTA ACCATGAGGA CCAGGTGTGT GTGTGGGGTG        476

GGCACATTGA TCTGGGATCG GGCCTGAGGT TTGCAGCATT TAGACCCTGC ATTTATAGCA        536

TACGGTATGA TATTGCAGCT TATATTCATC CATGCCCTGT ACCTGTGCAC GTTGGAACTT        596

TTATTACTGG GGTTTTCTA  AGAAAGAAAT TGTATTATCA ACAGCATTTT CAAGCAGTTA        656

GTTCCTTCAT GATCATCACA ATCATCATCA TTCTCATTCT CATTTTTTAA ATCAACGAGT        716
```

```
ACTTCAAGAT CTGAATTTGG CTTGTTTGGA GCATCTCCTC TGCTCCCCTG GGGAGTCTGG      776

GCACAGTCAG GTGGTGGCTT AACAGGGAGC TGGAAAAAGT GTCCTTTCTT CAGACACTGA      836

GGCTCCCGCA GCAGCGCCCC TCCCAAGAGG AAGGCCTCTG TGGCACTCAG ATACCGACTG      896

GGGCTGGGGC GCCGCCACTG CCTTCACCTC CTCTTTCAAA CCTCAGTGAT GGCTCTGTG      956

GGCTCCATGT AGAAGCCACT ATTACTGGGA CTGTCTCAGA GACCCCTCTC CCAGCTATTC      1016

CTACTCTCTC CCCGACTCCG AGAGCATGCT TAATCTTGCT TCTGCTTCTC ATTTCTGTAG      1076

CCTGATCAGC GCCGCACCAG CCGGGAAGAG GGTGATTGCT GGGGCTCGTG CCCTGCATCC      1136

CTCTCCTCCC AGGGCCTGCC CCACAGCTCG GGCCCTCTGT GAGATCCGTC TTTGGCCTCC      1196

TCCAGAATGG AGCTGGCCCT CTCCTGGGGA TGTGTAATGG TCCCCCTGCT TACCCGCAAA      1256

AGACAAGTCT TTACAGAATC AAATGCAATT TTAAATCTGA GAGCTCGCTT GAGTGACTGG      1316

GTTTGTGATT GCCTCTGAAG CCTATGTATG CCATGGAGGC ACTAACAAAC TCTGAGGTTT      1376

CCGAAATCAG AAGCGAAAAA ATCAGTGAAT AAACCATCAT CTTGCCACTA CCCCCTCCTG      1436

AAGCCACAGC AGGGGTTCAG GTTCCAATCA GAACTGTTGG CAAGGTGACA TTTCCATGCA      1496

TAGATGCGAT CCACAGAAGG TCCTGGTGGT ATTTGTAACT TTTTGCAAGG CATTTTTTA      1556

TATATATTTT TGTGCACATT TTTTTTACG ATTCTTTAGA AAACAAATGT ATTTCAAAAT      1616

ATATTTATAG TCGAACAAGT CATATATATG AATGAGAGCC ATATGAATGT CAGTAGTTTA      1676

TACTTCTCTA TTATCTCAAA CTACTGGCAA TTTGTAAAGA AATATATATG ATATATAAAT      1736

GTGATTGCAG CTTTTCAATG TTAGCCACAG TGTATTTTTT CACTTGTACT AAAATTGTAT      1796

CAAATGTGAC ATTATATGCA CTAGCAATAA AATGCTAATT GTTTCATGGT AAAAAAAAAA      1856
```

( 2 ) INFORMATION FOR SEQ ID NO:5:

( i ) SEQUENCE CHARACTERISTICS:
  ( A ) LENGTH: 93 amino acids
  ( B ) TYPE: amino acid
  ( D ) TOPOLOGY: linear  ( i i ) MOLECULE TYPE: protein  ( x i ) SEQUENCE DESCRIPTION: SEQ ID NO:5:

```
Met Asn Ala Lys Val Val Val Val Leu Val Leu Val Leu Thr Ala Leu
 1               5                  10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90
```

( 2 ) INFORMATION FOR SEQ ID NO:6:

( i ) SEQUENCE CHARACTERISTICS:
  ( A ) LENGTH: 279 base pairs
  ( B ) TYPE: nucleic acid
  ( C ) STRANDEDNESS: single
  ( D ) TOPOLOGY: linear  ( i i ) MOLECULE TYPE: cDNA to mRNA  ( x i ) SEQUENCE DESCRIPTION: SEQ ID NO:6:

| | | | | | |
|---|---|---|---|---|---|
| ATGAACGCCA | AGGTCGTGGT | CGTGCTGGTC | CTCGTGCTGA | CCGCGCTCTG | CCTCAGCGAC | 60 |
| GGGAAGCCCG | TCAGCCTGAG | CTACAGATGC | CCATGCCGAT | TCTTCGAAAG | CCATGTTGCC | 120 |
| AGAGCCAACG | TCAAGCATCT | CAAAATTCTC | AACACTCCAA | ACTGTGCCCT | TCAGATTGTA | 180 |
| GCCCGGCTGA | AGAACAACAA | CAGACAAGTG | TGCATTGACC | CGAAGCTAAA | GTGGATTCAG | 240 |
| GAGTACCTGG | AGAAAGCTTT | AAACAAGAGG | TTCAAGATG | | | 279 |

( 2 ) INFORMATION FOR SEQ ID NO:7:

( i ) SEQUENCE CHARACTERISTICS:
  ( A ) LENGTH: 3526 base pairs
  ( B ) TYPE: nucleic acid
  ( C ) STRANDEDNESS: single
  ( D ) TOPOLOGY: linear  ( i i ) MOLECULE TYPE: cDNA to mRNA  ( x i ) SEQUENCE DESCRIPTION: SEQ ID NO:7:

| | | | | | |
|---|---|---|---|---|---|
| TCTCCGTCAG | CCGCATTGCC | CGCTCGGCGT | CCGGCCCCG | ACCCGTGCTC | GTCCGCCCGC | 60 |
| CCGCCCGCCC | GCCCGCGCCA | TGAACGCCAA | GGTCGTGGTC | GTGCTGGTCC | TCGTGCTGAC | 120 |
| CGCGCTCTGC | CTCAGCGACG | GGAAGCCCGT | CAGCCTGAGC | TACAGATGCC | CATGCCGATT | 180 |
| CTTCGAAAGC | CATGTTGCCA | GAGCCAACGT | CAAGCATCTC | AAAATTCTCA | ACACTCCAAA | 240 |
| CTGTGCCCTT | CAGATTGTAG | CCCGGCTGAA | GAACAACAAC | AGACAAGTGT | GCATTGACCC | 300 |
| GAAGCTAAAG | TGGATTCAGG | AGTACCTGGA | GAAAGCTTTA | AACAAGAGGT | TCAAGATGTG | 360 |
| AGAGGGTCAG | ACGCCTGAGG | AACCCTTACA | GTAGGAGCCC | AGCTCTGAAA | CCAGTGTTAG | 420 |
| GGAAGGGCCT | GCCACAGCCT | CCCCTGCCAG | GGCAGGGCCC | CAGGCATTGC | CAAGGGCTTT | 480 |
| GTTTTGCACA | CTTTGCCATA | TTTTCACCAT | TTGATTATGT | AGCAAAATAC | ATGACATTTA | 540 |
| TTTTTCATTT | AGTTTGATTA | TTCAGTGTCA | CTGGCGACAC | GTAGCAGCTT | AGACTAAGGC | 600 |
| CATTATTGTA | CTTGCCTTAT | TAGAGTGTCT | TTCCACGGAG | CCACTCCTCT | GACTCAGGGC | 660 |
| TCCTGGGTTT | TGTATTCTCT | GAGCTGTGCA | GGTGGGGAGA | CTGGGCTGAG | GGAGCCTGGC | 720 |
| CCCATGGTCA | GCCCTAGGGT | GGAGAGCCAC | CAAGAGGGAC | GCCTGGGGGT | GCCAGGACCA | 780 |
| GTCAACCTGG | GCAAAGCCTA | GTGAAGGCTT | CTCTCTGTGG | GATGGGATGG | TGGAGGGCCA | 840 |
| CATGGGAGGC | TCACCCCCTT | CTCCATCCAC | ATGGGAGCCG | GGTCTGCCTC | TTCTGGGAGG | 900 |
| GCAGCAGGGC | TACCCTGAGC | TGAGGCAGCA | GTGTGAGGCC | AGGGCAGAGT | GAGACCCAGC | 960 |
| CCTCATCCCG | AGCACCTCCA | CATCCTCCAC | GTTCTGCTCA | TCATTCTCTG | TCTCATCCAT | 1020 |
| CATCATGTGT | GTCCACGACT | GTCTCCATGG | CCCCGCAAAA | GGACTCTCAG | GACCAAAGCT | 1080 |
| TTCATGTAAA | CTGTGCACCA | AGCAGGAAAT | GAAAATGTCT | TGTGTTACCT | GAAAACACTG | 1140 |
| TGCACATCTG | TGTCTTGTGT | GGAATATTGT | CCATTGTCCA | ATCCTATGTT | TTTGTTCAAA | 1200 |
| GCCAGCGTCC | TCCTCTGTGA | CCAATGTCTT | GATGCATGCA | CTGTTCCCCC | TGTGCAGCCG | 1260 |
| CTGAGCGAGG | AGATGCTCCT | TGGGCCCTTT | GAGTGCAGTC | CTGATCAGAG | CCGTGGTCCT | 1320 |
| TTGGGGTGAA | CTACCTTGGT | TCCCCACTG | ATCACAAAAA | CATGGTGGGT | CCATGGGCAG | 1380 |
| AGCCCAAGGG | AATTCGGTGT | GCACCAGGGT | TGACCCAGA | GGATTGCTGC | CCCATCAGTG | 1440 |
| CTCCCTCACA | TGTCAGTACC | TTCAAACTAG | GGCCAAGCCC | AGCACTGCTT | GAGGAAAACA | 1500 |
| AGCATTCACA | ACTTGTTTTT | GGTTTTAAA | ACCCAGTCCA | CAAATAACC | AATCCTGGAC | 1560 |
| ATGAAGATTC | TTTCCCAATT | CACATCTAAC | CTCATCTTCT | TCACCATTTG | GCAATGCCAT | 1620 |
| CATCTCCTGC | CTTCCTCCTG | GGCCCTCTCT | GCTCTGCGTG | TCACCTGTGC | TTCGGGCCCT | 1680 |

-continued

| | | | | | |
|---|---|---|---|---|---|
| TCCCACAGGA | CATTTCTCTA | AGAGAACAAT | GTGCTATGTG | AAGAGTAAGT | CAACCTGCCT | 1740 |
| GACATTTGGA | GTGTTCCCCT | CCCACTGAGG | GCAGTCGATA | GAGCTGTATT | AAGCCACTTA | 1800 |
| AAATGTTCAC | TTTTGACAAA | GGCAAGCACT | TGTGGGTTTT | TGTTTTGTTT | TTCATTCAGT | 1860 |
| CTTACGAATA | CTTTTGCCCT | TTGATTAAAG | ACTCCAGTTA | AAAAAAATTT | TAATGAAGAA | 1920 |
| AGTGGAAAAC | AAGGAAGTCA | AGCAAGGAA | ACTATGTAAC | ATGTAGGAAG | TAGGAAGTAA | 1980 |
| ATTATAGTGA | TGTAATCTTG | AATTGTAACT | GTTCGTGAAT | TTAATAATCT | GTAGGGTAAT | 2040 |
| TAGTAACATG | TGTTAAGTAT | TTTCATAAGT | ATTTCAAATT | GGAGCTTCAT | GGCAGAAGGC | 2100 |
| AAACCCATCA | ACAAAAATTG | TCCCTTAAAC | AAAAATTAAA | ATCCTCAATC | CAGCTATGTT | 2160 |
| ATATTGAAAA | AATAGAGCCT | GAGGGATCTT | TACTAGTTAT | AAAGATACAG | AACTCTTTCA | 2220 |
| AAACCTTTTG | AAATTAACCT | CTCACTATAC | CAGTATAATT | GAGTTTTCAG | TGGGGCAGTC | 2280 |
| ATTATCCAGG | TAATCCAAGA | TATTTTAAAA | TCTGTCACGT | AGAACTTGGA | TGTACCTGCC | 2340 |
| CCCAATCCAT | GAACCAAGAC | CATTGAATTC | TTGGTTGAGG | AAACAAACAT | GACCCTAAAT | 2400 |
| CTTGACTACA | GTCAGGAAAG | GAATCATTTC | TATTTCTCCT | CCATGGGAGA | AAATAGATAA | 2460 |
| GAGTAGAAAC | TGCAGGGAAA | ATTATTTGCA | TAACAATTCC | TCTACTAACA | ATCAGCTCCT | 2520 |
| TCCTGGAGAC | TGCCCAGCTA | AAGCAATATG | CATTTAAATA | CAGTCTTCCA | TTTGCAAGGG | 2580 |
| AAAAGTCTCT | TGTAATCCGA | ATCTCTTTTT | GCTTTCGAAC | TGCTAGTCAA | GTGCGTCCAC | 2640 |
| GAGCTGTTTA | CTAGGGATCC | CTCATCTGTC | CCTCCGGGAC | CTGGTGCTGC | CTCTACCTGA | 2700 |
| CACTCCCTTG | GGCTCCCTGT | AACCTCTTCA | GAGGCCCTCG | CTGCCAGCTC | TGTATCAGGA | 2760 |
| CCCAGAGGAA | GGGGCCAGAG | GCTCGTTGAC | TGGCTGTGTG | TTGGGATTGA | GTCTGTGCCA | 2820 |
| CGTGTATGTG | CTGTGGTGTG | TCCCCCTCTG | TCCAGGCACT | GAGATACCAG | CGAGGAGGCT | 2880 |
| CCAGAGGGCA | CTCTGCTTGT | TATTAGAGAT | TACCTCCTGA | GAAAAAAGCT | TCCGCTTGGA | 2940 |
| GCAGAGGGGC | TGAATAGCAG | AAGGTTGCAC | CTCCCCCAAC | CTTAGATGTT | CTAAGTCTTT | 3000 |
| CCATTGGATC | TCATTGGACC | CTTCCATGGT | GTGATCGTCT | GACTGGTGTT | ATCACCGTGG | 3060 |
| GCTCCCTGAC | TGGGAGTTGA | TCGCCTTTCC | CAGGTGCTAC | ACCCTTTTCC | AGCTGGATGA | 3120 |
| GAATTTGAGT | GCTCTGATCC | CTCTACAGAG | CTTCCCTGAC | TCATTCTGAA | GGAGCCCCAT | 3180 |
| TCCTGGGAAA | TATTCCCTAG | AAACTTCCAA | ATCCCCTAAG | CAGACCACTG | ATAAAACCAT | 3240 |
| GTAGAAAATT | TGTTATTTTG | CAACCTCGCT | GGACTCTCAG | TCTCTGAGCA | GTGAATGATT | 3300 |
| CAGTGTTAAA | TGTGATGAAT | ACTGTATTTT | GTATTGTTTC | AAGTGCATCT | CCCAGATAAT | 3360 |
| GTGAAAATGG | TCCAGGAGAA | GGCCAATTCC | TATACGCAGC | GTGCTTTAAA | AAATAAATAA | 3420 |
| GAAACAACTC | TTTGAGAAAC | AACAATTTCT | ACTTTGAAGT | CATACCAATG | AAAAAATGTA | 3480 |
| TATGCACTTA | TAATTTTCCT | AATAAAGTTC | TGTACTCAAA | TGTAAA | | 3526 |

( 2 ) INFORMATION FOR SEQ ID NO:8:

( i ) SEQUENCE CHARACTERISTICS:
        ( A ) LENGTH: 3526 base pairs
        ( B ) TYPE: nucleic acid
        ( C ) STRANDEDNESS: single
        ( D ) TOPOLOGY: linear     ( i i ) MOLECULE TYPE: cDNA to mRNA     ( v i ) ORIGINAL SOURCE:
        ( A ) ORGANISM: Homo sapiens
        ( H ) CELL LINE: FLEB14

( i x ) FEATURE:
        ( A ) NAME/KEY: CDS
        ( B ) LOCATION: 80..361

( C ) IDENTIFICATION METHOD: by similarity to some other pattern ( i x ) FEATURE:
    ( A ) NAME/KEY: sig_peptide
    ( B ) LOCATION: 80..142
    ( C ) IDENTIFICATION METHOD: by similarity with known sequence or to an established consensus ( i x ) FEATURE:
    ( A ) NAME/KEY: mat_peptide
    ( B ) LOCATION: 143..358
    ( C ) IDENTIFICATION METHOD: by similarity with known sequence or to an established consensus ( x i ) SEQUENCE DESCRIPTION: SEQ ID NO:8:

```
TCTCCGTCAG CCGCATTGCC CGCTCGGCGT CCGGCCCCCG ACCCGTGCTC GTCCGCCCGC                    60

CCGCCCGCCC GCCCGCGCC ATG AAC GCC AAG GTC GTG GTC GTG CTG GTC CTC                    112
                    Met Asn Ala Lys Val Val Val Val Leu Val Leu
                    -21 -20                      -15

GTG CTG ACC GCG CTC TGC CTC AGC GAC GGG AAG CCC GTC AGC CTG AGC                      160
Val Leu Thr Ala Leu Cys Leu Ser Asp Gly Lys Pro Val Ser Leu Ser
-10              -5                   1                    5

TAC AGA TGC CCA TGC CGA TTC TTC GAA AGC CAT GTT GCC AGA GCC AAC                      208
Tyr Arg Cys Pro Cys Arg Phe Phe Glu Ser His Val Ala Arg Ala Asn
              10                  15                      20

GTC AAG CAT CTC AAA ATT CTC AAC ACT CCA AAC TGT GCC CTT CAG ATT                      256
Val Lys His Leu Lys Ile Leu Asn Thr Pro Asn Cys Ala Leu Gln Ile
          25                  30                  35

GTA GCC CGG CTG AAG AAC AAC AAC AGA CAA GTG TGC ATT GAC CCG AAG                      304
Val Ala Arg Leu Lys Asn Asn Asn Arg Gln Val Cys Ile Asp Pro Lys
        40                  45                  50

CTA AAG TGG ATT CAG GAG TAC CTG GAG AAA GCT TTA AAC AAG AGG TTC                      352
Leu Lys Trp Ile Gln Glu Tyr Leu Glu Lys Ala Leu Asn Lys Arg Phe
55                  60                  65                  70

AAG ATG TGAGAGGGTC AGACGCCTGA GGAACCCTTA CAGTAGGAGC CCAGCTCTGA                        408
Lys Met

AACCAGTGTT AGGGAAGGGC CTGCCACAGC CTCCCTGCC AGGGCAGGGC CCAGGCATT                        468

GCCAAGGGCT TTGTTTTGCA CACTTTGCCA TATTTTCACC ATTTGATTAT GTAGCAAAAT                      528

ACATGACATT TATTTTTCAT TTAGTTTGAT TATTCAGTGT CACTGGCGAC ACGTAGCAGC                       588

TTAGACTAAG GCCATTATTG TACTTGCCTT ATTAGAGTGT CTTTCCACGG AGCCACTCCT                       648

CTGACTCAGG GCTCCTGGGT TTTGTATTCT CTGAGCTGTG CAGGTGGGGA GACTGGGCTG                       708

AGGGAGCCTG GCCCCATGGT CAGCCCTAGG GTGGAGAGCC ACCAAGAGGG ACGCCTGGGG                       768

GTGCCAGGAC CAGTCAACCT GGGCAAAGCC TAGTGAAGGC TTCTCTCTGT GGGATGGGAT                       828

GGTGGAGGGC CACATGGGAG GCTCACCCCC TTCTCCATCC ACATGGGAGC CGGGTCTGCC                       888

TCTTCTGGGA GGGCAGCAGG GCTACCCTGA GCTGAGGCAG CAGTGTGAGG CCAGGGCAGA                       948

GTGAGACCCA GCCCTCATCC CGAGCACCTC CACATCCTCC ACGTTCTGCT CATCATTCTC                      1008

TGTCTCATCC ATCATCATGT GTGTCCACGA CTGTCTCCAT GGCCCCGCAA AAGGACTCTC                      1068

AGGACCAAAG CTTTCATGTA AACTGTGCAC CAAGCAGGAA ATGAAAATGT CTTGTGTTAC                      1128

CTGAAAACAC TGTGCACATC TGTGTCTTGT GTGGAATATT GTCCATTGTC CAATCCTATG                      1188

TTTTTGTTCA AAGCCAGCGT CCTCCTCTGT GACCAATGTC TTGATGCATG CACTGTTCCC                      1248

CCTGTGCAGC CGCTGAGCGA GGAGATGCTC CTTGGGCCCT TGAGTGCAG TCCTGATCAG                       1308

AGCCGTGGTC CTTTGGGGTG AACTACCTTG GTTCCCCAC TGATCACAAA AACATGGTGG                       1368

GTCCATGGGC AGAGCCCAAG GGAATTCGGT GTGCACCAGG GTTGACCCCA GAGGATTGCT                      1428
```

| | | | | | |
|---|---|---|---|---|---|
| GCCCCATCAG | TGCTCCCTCA | CATGTCAGTA | CCTTCAAACT | AGGGCCAAGC | CCAGCACTGC | 1488 |
| TTGAGGAAAA | CAAGCATTCA | CAACTTGTTT | TTGGTTTTTA | AAACCCAGTC | CACAAAATAA | 1548 |
| CCAATCCTGG | ACATGAAGAT | TCTTTCCCAA | TTCACATCTA | ACCTCATCTT | CTTCACCATT | 1608 |
| TGGCAATGCC | ATCATCTCCT | GCCTTCCTCC | TGGGCCCTCT | CTGCTCTGCG | TGTCACCTGT | 1668 |
| GCTTCGGGCC | CTTCCACAG | GACATTTCTC | TAAGAGAACA | ATGTGCTATG | TGAAGAGTAA | 1728 |
| GTCAACCTGC | CTGACATTTG | GAGTGTTCCC | CTCCCACTGA | GGGCAGTCGA | TAGAGCTGTA | 1788 |
| TTAAGCCACT | TAAAATGTTC | ACTTTGACA | AAGGCAAGCA | CTTGTGGGTT | TTTGTTTTGT | 1848 |
| TTTTCATTCA | GTCTTACGAA | TACTTTGCC | CTTGATTAA | AGACTCCAGT | TAAAAAAAAT | 1908 |
| TTTAATGAAG | AAAGTGGAAA | ACAAGGAAGT | CAAAGCAAGG | AAACTATGTA | ACATGTAGGA | 1968 |
| AGTAGGAAGT | AAATTATAGT | GATGTAATCT | TGAATTGTAA | CTGTTCGTGA | ATTTAATAAT | 2028 |
| CTGTAGGGTA | ATTAGTAACA | TGTGTTAAGT | ATTTTCATAA | GTATTTCAAA | TTGGAGCTTC | 2088 |
| ATGGCAGAAG | GCAAACCCAT | CAACAAAAAT | TGTCCCTTAA | ACAAAAATTA | AAATCCTCAA | 2148 |
| TCCAGCTATG | TTATATTGAA | AAAATAGAGC | CTGAGGGATC | TTTACTAGTT | ATAAAGATAC | 2208 |
| AGAACTCTTT | CAAAACCTTT | TGAAATTAAC | CTCTCACTAT | ACCAGTATAA | TTGAGTTTTC | 2268 |
| AGTGGGGCAG | TCATTATCCA | GGTAATCCAA | GATATTTTAA | AATCTGTCAC | GTAGAACTTG | 2328 |
| GATGTACCTG | CCCCCAATCC | ATGAACCAAG | ACCATTGAAT | TCTTGGTTGA | GGAAACAAAC | 2388 |
| ATGACCCTAA | ATCTTGACTA | CAGTCAGGAA | AGGAATCATT | TCTATTTCTC | CTCCATGGGA | 2448 |
| GAAAATAGAT | AAGAGTAGAA | ACTGCAGGGA | AAATTATTTG | CATAACAATT | CCTCTACTAA | 2508 |
| CAATCAGCTC | CTTCCTGGAG | ACTGCCCAGC | TAAAGCAATA | TGCATTTAAA | TACAGTCTTC | 2568 |
| CATTTGCAAG | GGAAAAGTCT | CTTGTAATCC | GAATCTCTTT | TTGCTTTCGA | ACTGCTAGTC | 2628 |
| AAGTGCGTCC | ACGAGCTGTT | TACTAGGGAT | CCCTCATCTG | TCCCTCCGGG | ACCTGGTGCT | 2688 |
| GCCTCTACCT | GACACTCCCT | TGGGCTCCCT | GTAACCTCTT | CAGAGGCCCT | CGCTGCCAGC | 2748 |
| TCTGTATCAG | GACCCAGAGG | AAGGGGCCAG | AGGCTCGTTG | ACTGGCTGTG | TGTTGGGATT | 2808 |
| GAGTCTGTGC | CACGTGTATG | TGCTGTGGTG | TGTCCCCCTC | TGTCCAGGCA | CTGAGATACC | 2868 |
| AGCGAGGAGG | CTCCAGAGGG | CACTCTGCTT | GTTATTAGAG | ATTACCTCCT | GAGAAAAAAG | 2928 |
| CTTCCGCTTG | GAGCAGAGGG | GCTGAATAGC | AGAAGGTTGC | ACCTCCCCA | ACCTTAGATG | 2988 |
| TTCTAAGTCT | TTCCATTGGA | TCTCATTGGA | CCCTTCCATG | GTGTGATCGT | CTGACTGGTG | 3048 |
| TTATCACCGT | GGGCTCCCTG | ACTGGGAGTT | GATCGCCTTT | CCCAGGTGCT | ACACCCTTTT | 3108 |
| CCAGCTGGAT | GAGAATTTGA | GTGCTCTGAT | CCCTCTACAG | AGCTTCCCTG | ACTCATTCTG | 3168 |
| AAGGAGCCCC | ATTCCTGGGA | AATATTCCCT | AGAAACTTCC | AAATCCCCTA | AGCAGACCAC | 3228 |
| TGATAAAACC | ATGTAGAAAA | TTTGTTATTT | TGCAACCTCG | CTGGACTCTC | AGTCTCTGAG | 3288 |
| CAGTGAATGA | TTCAGTGTTA | AATGTGATGA | ATACTGTATT | TTGTATTGTT | TCAAGTGCAT | 3348 |
| CTCCCAGATA | ATGTGAAAAT | GGTCCAGGAG | AAGGCCAATT | CCTATACGCA | GCGTGCTTTA | 3408 |
| AAAAATAAAT | AAGAAACAAC | TCTTTGAGAA | ACAACAATTT | CTACTTTGAA | GTCATACCAA | 3468 |
| TGAAAAAATG | TATATGCACT | TATAATTTTC | CTAATAAAGT | TCTGTACTCA | AATGTAAA | 3526 |

( 2 ) INFORMATION FOR SEQ ID NO:9:

( i ) SEQUENCE CHARACTERISTICS:
        ( A ) LENGTH: 1797 base pairs
        ( B ) TYPE: nucleic acid
        ( C ) STRANDEDNESS: single
        ( D ) TOPOLOGY: linear     ( i i ) MOLECULE TYPE: cDNA to mRNA ( x i ) SEQUENCE DESCRIPTION: SEQ ID NO:9:

| | | | | | | |
|---|---|---|---|---|---|---|
| GACCACTTTC | CCTCTCGGTC | CACCTCGGTG | TCCTCTTGCT | GTCCAGCTCT | GCAGCCTCCG | 60 |
| GCGCGCCCTC | CCGCCCACGC | CATGGACGCC | AAGGTCGTCG | CCGTGCTGGC | CCTGGTGCTG | 120 |
| GCCGCGCTCT | GCATCAGTGA | CGGTAAACCA | GTCAGCCTGA | GCTACCGATG | CCCCTGCCGG | 180 |
| TTCTTCGAGA | GCCACATCGC | CAGAGCCAAC | GTCAAGCATC | TGAAAATCCT | CAACACTCCA | 240 |
| AACTGTGCCC | TTCAGATTGT | TGCACGGCTG | AAGAACAACA | ACAGACAAGT | GTGCATTGAC | 300 |
| CCGAAATTAA | AGTGGATCCA | AGAGTACCTG | GAGAAAGCTT | TAAACAAGTA | AGCACAACAG | 360 |
| CCCAAAGGAC | TTTCCAGTAG | ACCCCGAGG | AAGGCTGACA | TCCGTGGGAG | ATGCAAGGGC | 420 |
| AGTGGTGGGG | AGGAGGGCCT | GAACCCTGGC | CAGGATGGCC | GGCGGGACAG | CACTGACTGG | 480 |
| GGTCATGCTA | AGGTTTGCCA | GCATAAAGAC | ACTCCGCCAT | AGCATATGGT | ACGATATTGC | 540 |
| AGCTTATATT | CATCCCTGCC | CTCGCCCGTG | CACAATGGAG | CTTTTATAAC | TGGGGTTTTT | 600 |
| CTAAGGAATT | GTATTACCCT | AACCAGTTAG | CTTCATCCCC | ATTCTCCTCA | TCCTCATCTT | 660 |
| CATTTTAAAA | AGCAGTGATT | ACTTCAAGGG | CTGTATTCAG | TTTGCTTTGG | AGCTTCTCTT | 720 |
| TGCCCTGGGG | CCTCTGGGCA | CAGTTATAGA | CGGTGGCTTT | GCAGGAGCC | CTAGAGAGAA | 780 |
| ACCTTCCACC | AGAGCAGAGT | CCGAGGAACG | CTGCAGGGCT | TGTCCTGCAG | GGGGCGCTCC | 840 |
| TCGACAGATG | CCTTGTCCTG | AGTCAACACA | AGATCCGGCA | GAGGGAGGCT | CCTTTATCCA | 900 |
| GTTCAGTGCC | AGGGTCGGGA | AGCTTCCTTT | AGAAGTGATC | CCTGAAGCTG | TGCTCAGAGA | 960 |
| CCCTTTCCTA | GCCGTTCCTG | CTCTCTGCTT | GCCTCCAAAC | GCATGCTTCA | TCTGACTTCC | 1020 |
| GCTTCTCACC | TCTGTAGCCT | GACGGACCAA | TGCTGCAATG | GAAGGGAGGA | GAGTGATGTG | 1080 |
| GGGTGCCCCC | TCCCTCTCTT | CCCTTTGCTT | TCCTCTCACT | TGGGCCCTTT | GTGAGATTTT | 1140 |
| TCTTTGGCCT | CCTGTAGAAT | GGAGCCAGAC | CATCCTGGAT | AATGTGAGAA | CATGCCTAGA | 1200 |
| TTTACCCACA | AAACACAAGT | CTGAGAATTA | ATCATAAACG | GAAGTTTAAA | TGAGGATTTG | 1260 |
| GACCTTGGTA | ATTGTCCCTG | AGTCCTATAT | ATTTCAACAG | TGGCTCTATG | GGCTCTGATC | 1320 |
| GAATATCAGT | GATGAAAATA | ATAATAATAA | TAATAATAAC | GAATAAGCCA | GAATCTTGCC | 1380 |
| ATGAAGCCAC | AGTGGGGATT | CTGGGTTCCA | ATCAGAAATG | GAGACAAGAT | AAAACTTGCA | 1440 |
| TACATTCTTA | TGATCACAGA | CGGCCCTGGT | GGTTTTTGGT | AACTATTTAC | AAGGCATTTT | 1500 |
| TTTACATATA | TTTTTGTGCA | CTTTTTATGT | TTCTTTGGAA | GACAAATGTA | TTTCAGAATA | 1560 |
| TATTTGTAGT | CAATTCATAT | ATTTGAAGTG | GAGCCATAGT | AATGCCAGTA | GATATCTCTA | 1620 |
| TGATCTTGAG | CTACTGGCAA | CTTGTAAAGA | AATATATATG | ACATATAAAT | GTATTGTAGC | 1680 |
| TTTCCGGTGT | CAGCCACGGT | GTATTTTTCC | ACTTGGAATG | AAATTGTATC | AACTGTGACA | 1740 |
| TTATATGCAC | TAGCAATAAA | ATGCTAATTG | TTTCATGCTG | TAAAAAAAAA | AAAAAAA | 1797 |

( 2 ) INFORMATION FOR SEQ ID NO:10:

( i ) SEQUENCE CHARACTERISTICS:
( A ) LENGTH: 14 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:10:

AATTCGCGGC CGCT    14

( 2 ) INFORMATION FOR SEQ ID NO:11:

( i ) SEQUENCE CHARACTERISTICS:
   ( A ) LENGTH: 10 base pairs
   ( B ) TYPE: nucleic acid
   ( C ) STRANDEDNESS: double
   ( D ) TOPOLOGY: linear ( i i ) MOLECULE TYPE: cDNA ( i x ) FEATURE:
   ( A ) NAME/KEY: misc_feature
   ( B ) LOCATION: 1
   ( D ) OTHER INFORMATION: /label=phosphorylated ( x i ) SEQUENCE DESCRIPTION: SEQ ID NO:11:

AGCGGCCGCG                                                                                                    10

( 2 ) INFORMATION FOR SEQ ID NO:12:

( i ) SEQUENCE CHARACTERISTICS:
      ( A ) LENGTH: 28 base pairs
      ( B ) TYPE: nucleic acid
      ( C ) STRANDEDNESS: double
      ( D ) TOPOLOGY: linear ( i i ) MOLECULE TYPE: DNA (synthetic)

( x i ) SEQUENCE DESCRIPTION: SEQ ID NO:12:

GTAATACGAC TCACTATAGG GGAGAGCT                                                                                28

( 2 ) INFORMATION FOR SEQ ID NO:13:

( i ) SEQUENCE CHARACTERISTICS:
      ( A ) LENGTH: 28 base pairs
      ( B ) TYPE: nucleic acid
      ( C ) STRANDEDNESS: double
      ( D ) TOPOLOGY: linear ( i i ) MOLECULE TYPE: DNA (synthetic)

( x i ) SEQUENCE DESCRIPTION: SEQ ID NO:13:

CTCCCCTATA GTGAGTCGTA TTACTGCA                                                                                28

( 2 ) INFORMATION FOR SEQ ID NO:14:

( i ) SEQUENCE CHARACTERISTICS:
      ( A ) LENGTH: 32 base pairs
      ( B ) TYPE: nucleic acid
      ( C ) STRANDEDNESS: double
      ( D ) TOPOLOGY: linear ( i i ) MOLECULE TYPE: DNA (synthetic)

( x i ) SEQUENCE DESCRIPTION: SEQ ID NO:14:

CTAGTCTATA GTGTCACCTA AATCGTGGGT AC                                                                           32

( 2 ) INFORMATION FOR SEQ ID NO:15:

( i ) SEQUENCE CHARACTERISTICS:
      ( A ) LENGTH: 23 base pairs
      ( B ) TYPE: nucleic acid
      ( C ) STRANDEDNESS: double
      ( D ) TOPOLOGY: linear ( i i ) MOLECULE TYPE: DNA (synthetic)

( x i ) SEQUENCE DESCRIPTION: SEQ ID NO:15:

CACGATTTAG GTGACACTAT AGA                                                                                     23

( 2 ) INFORMATION FOR SEQ ID NO:16:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:16:

AATATAGTCG ACCACCATGA ACGCCAAGGT CGTGGTCGTG CTGG    44

( 2 ) INFORMATION FOR SEQ ID NO:17:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear  ( i i ) MOLECULE TYPE: DNA (synthetic)

( x i ) SEQUENCE DESCRIPTION: SEQ ID NO:17:

CGGCGGACTA GTTTACTTGT TTAAAGCTTT CTCCAGG    37

( 2 ) INFORMATION FOR SEQ ID NO:18:

( i ) SEQUENCE CHARACTERISTICS:
  ( A ) LENGTH: 55 base pairs
  ( B ) TYPE: nucleic acid
  ( C ) STRANDEDNESS: single
  ( D ) TOPOLOGY: linear  ( i i ) MOLECULE TYPE: DNA (synthetic)

( x i ) SEQUENCE DESCRIPTION: SEQ ID NO:18:

GCCGCCACTA GTTTAGTGGT GGTGGTGGTG GTGCTTGTTT AAAGCTTTCT CCAGG    55

( 2 ) INFORMATION FOR SEQ ID NO:19:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear  ( i i ) MOLECULE TYPE: DNA (synthetic)

( x i ) SEQUENCE DESCRIPTION: SEQ ID NO:19:

CGGCGGACTA GTTCACATCT TGAACCTCTT GTTTAAAGC    39

( 2 ) INFORMATION FOR SEQ ID NO:20:

( i ) SEQUENCE CHARACTERISTICS:
  ( A ) LENGTH: 57 base pairs
  ( B ) TYPE: nucleic acid
  ( C ) STRANDEDNESS: single
  ( D ) TOPOLOGY: linear  ( i i ) MOLECULE TYPE: DNA (synthetic)

( x i ) SEQUENCE DESCRIPTION: SEQ ID NO:20:

GCCGCCACTA GTTCAGTGGT GGTGGTGGTG GTGCATCTTG AACCTCTTGT TTAAAGC    57